(12) United States Patent
Shimada

(10) Patent No.: US 8,105,637 B2
(45) Date of Patent: Jan. 31, 2012

(54) **COMPOSITION COMPRISING NANOPARTICLE *GINKGO BILOBA* EXTRACT WITH THE EFFECT OF BRAIN FUNCTION ACTIVATION**

(76) Inventor: Shinji Shimada, Okegawa (JP)

( * ) Notice: Subject to any disclaimer, the term of this patent is extended or adjusted under 35 U.S.C. 154(b) by 524 days.

(21) Appl. No.: 11/688,487

(22) Filed: Mar. 20, 2007

(65) Prior Publication Data

US 2008/0254126 A1 Oct. 16, 2008

(51) Int. Cl.
*A61K 36/16* (2006.01)
*A61K 9/14* (2006.01)

(52) U.S. Cl. .......................... 424/752; 424/489

(58) Field of Classification Search .................. None
See application file for complete search history.

(56) References Cited

U.S. PATENT DOCUMENTS

| | | | | |
|---|---|---|---|---|
| 5,686,082 | A * | 11/1997 | N'Guyen ..................... | 424/752 |
| 6,117,431 | A * | 9/2000 | Ramazanov et al. ......... | 424/752 |
| 6,174,531 | B1 * | 1/2001 | Zhang et al. ................. | 424/752 |
| 6,221,356 | B1 * | 4/2001 | Junsheng ..................... | 424/752 |
| 2004/0028757 | A1 * | 2/2004 | Cals-Grierson et al. ...... | 424/757 |
| 2005/0118286 | A1 * | 6/2005 | Suffin et al. ................. | 424/752 |
| 2005/0258288 | A1 * | 11/2005 | Dalziel et al. ................ | 241/172 |
| 2006/0182821 | A1 * | 8/2006 | Drieu et al. .................. | 424/752 |

FOREIGN PATENT DOCUMENTS

| | | | |
|---|---|---|---|
| CN | 1314146 | * | 9/2001 |
| CN | 1314146 | A | 9/2001 |
| CN | 1362191 | * | 8/2002 |
| CN | 1362191 | A | 8/2002 |
| CN | 1397555 | A | 2/2003 |
| CN | 1465339 | A | 1/2004 |
| JP | 2003-95966 | A | 4/2003 |
| JP | 2006-25630 | A | 2/2006 |
| WO | WO 2004/000274 | * | 12/2003 |

OTHER PUBLICATIONS

Japanese Office Action, dated Dec. 12, 2006, in a counterpart Japanesse patent Application No. JP 2006-106821. Concise Explanation of Relevance: the Japanese Office Action rejects claims in the Japanese application in view of Foreign Patent Document Nos. 1-6 above and Non-Patent Literature No. 3 below.
Japanes Office Action, dated Apr. 12, 2007, in a counterpart Japanese patent application, No. JP 2006-106821. Concise Explanation of Relevance: the Japanese Office Action rejects claims in the Japanese application in view of Foreign Patent Document Nos. 1-6 above and Non-Patent Literature No. 3 below.
"Preparation and perfomance of the nanoLiuwei Dihuang solution", Ma et al., Chinese Journal of aterials Research, Aug. 2005, vol. 19, No. 4, pp. 413-418, English abstract included as a concise explanation of relevance.
"Mesh (scale)", Wikipedia, the free encyclopedia, http://en.wikipedia.org/wiki/Mesh_(scale), 6 pages, printed from the Internet on Dec. 27, 2010.

* cited by examiner

*Primary Examiner* — Christopher R. Tate
(74) *Attorney, Agent, or Firm* — Chen Yoshimura LLP

(57) ABSTRACT

To supply the *ginkgo biloba* extract which contains no ginkgolic acid but the active ingredient of existing *ginkgo biloba* extract and which achieves significant effects in activation of the brain cells. The composition comprises nanoparticle *ginkgo biloba* extract as the active ingredient, which has the effect of brain function activation. The *ginkgo biloba* extract is free of ginkgolic acid and is made with the breakdown method, the combination of dry and wet process, crushing *ginkgo biloba* extract powder. The nanoparticle is 100 nm and below. The above composition has the form from the group consisting of condiments, food additives, food materials, food and drink, health food and drink, drugs, quasi drugs and feeding stuffs. The above health food and drink is for patients with abnormality in cerebral blood flow and metabolism and with the effect of brain function activation prevents or improves the symptom. The above drugs and quasi drugs are intended for human or animal use.

5 Claims, 5 Drawing Sheets

Liver

Kidney

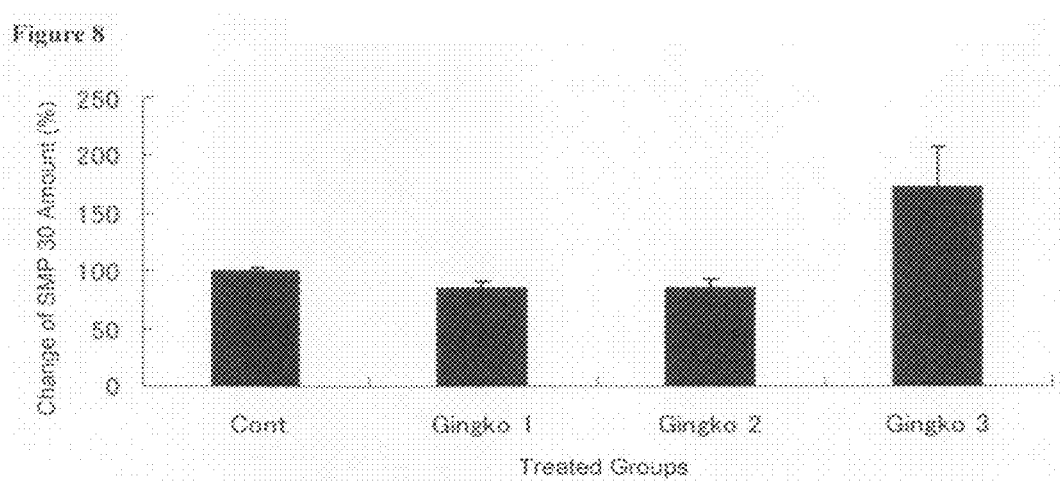

COMPOSITION COMPRISING NANOPARTICLE *GINKGO BILOBA* EXTRACT WITH THE EFFECT OF BRAIN FUNCTION ACTIVATION

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

The invention relates to the composition comprising nanoparticle *ginkgo biloba* extract with the effect of brain function activation.

*Ginkgo biloba* extract has been conventionally obtained as powder after *ginkgo biloba* extracted with alcohol is adsorbed to porous resin to be concentrated and dried at high heat. The extract of *ginkgo biloba* is recognized for comprising the active ingredient with pharmacological effects: restoring the weakened vessels by direct action on vessel wall and restoring flexibility of hardened vessels, decreasing peripheral resistance by thinning the thick blood, enhancing immune function or inhibiting platelet activator. It has been used extensively, especially in France or Germany, as a drug for improvement of cerebral blood flow and metabolism. Ginkgo extract is also consumed as food as can be seen from some health food claiming comprising it in the market. Ginkgo extract, additionally, in skin preparation is recognized for normalizing and promoting peripheral circulation under the skin and achieving significant cosmetic effects. As for useful components in *ginkgo biloba*, their effects are revealing; anti-stress ulcer effect of salicylic acid derivative (patent literature 1), blood pressure-lowering effect of flavone glycoside, specific to *ginkgo biloba* (nonpatent literature 1) or inhibitory effect of gikgolides on platelet activator has been reported.

However on the other hand, *ginkgo biloba* component contains ginkgolic acid which is a kind of hydrophobic, salicylic acid derivative causing allergy or polyphenolic compound (proanthocyanidin) with water solubility and browning reaction. They must be removed when *ginkgo biloba* extract is used in drugs, foods or cosmetic materials. The procedures of obtaining the extract with active ingredient of *ginkgo biloba* are generally acknowledged; they all employ the highly toxic, low-boiling and difficult-to-remove solvent so that the extract may not contain salicylic acid derivative or polyphenolic compound but may have high active ingredient of flavone glycoside and terpene lactones. The extraction procedure avoiding using highly toxic organic solvent is disclosed, which utilizes purification of the hydroalcoholic extract with porous nonpolar resin (patent literature 2 and 3). While this procedure provides the way to obtain *ginkgo biloba* extract only with the ethanol appropriate to food manufacturing, use of porous nonpolar resin has the drawback of requiring additional energy to its regeneration and solvent recovery.

Patent Literature 1: Kokai (unexamined patent publication) No. 63-215629 (1988-215629)
Patent Literature 2: Kokai (unexamined patent publication) No. 3-275629 (1991-275629)
Patent Literature 3: Kokai (unexamined patent publication) No. 4-182434 (1992-182434)
Nonpatent Literature 1: *Proceedings of the 107th Annual Meeting of the Pharmaceutical Society of Japan*, (in Japanese) p. 345

SUMMARY OF THE INVENTION

The *ginkgo biloba* extract powder existing in the marketplace contains ginkgolic acid, which induces allergy.

Moreover, the existing *ginkgo biloba* extract powder, whose plant cell wall remains undestructed, provides smaller amount of active ingredient.

Physically crushing method cannot shrink the organic substance down to nanosized particles and the large particles are unable to
  pass thorough the blood-brain barrier,
  penetrate into brain cells, nor
  reach the hippocampus,
because of which, it is unable to achieve significant effects in activation of the brain cells.

This invention is intended to supply the functional nanoparticle *ginkgo biloba* extract which has overcome the above issues, which contains no ginkgolic acid, the sensitizer causing contact dermatitis, but existing active ingredient of *ginkgo biloba* extract, and which achieves significant effects in activation of the brain cells.

The substance of this invention is the composition with the effect of brain function activation, the following 1) through 7).

1) The composition comprising nanoparticle *ginkgo biloba* extract as the active ingredient, which has the effect of brain function activation.
2) The composition with the effect of brain function activation as 1), which is ginkgolic acid free and is made with the breakdown method, the combination of dry and wet process, crushing *ginkgo biloba* extract powder.
3) The composition, nanoparticle of which is 100 nm and below and which has the effect of brain function activation as 1) or 2).
4) The composition with the effect of brain function activation as 1), 2) or 3), which has the form chosen from the group consisting of condiments, food additives, food materials, food and drink, health food and drink, drugs, quasi drugs and feeding stuffs.
5) The composition with the effect of brain function activation as 4), which is of the above health food and drink and for patients with abnormality in cerebral blood flow and metabolism and with whose effect of brain function activation prevents or improves the symptom.
6) The composition with the effect of brain function activation as 4), which is of the above drugs and quasi drugs and is intended for human or animal use.
7) The composition with the effect of brain function activation as 1) or 6), with whose effect of brain function activation prevents or improves the symptom of abnormality in cerebral blood flow and metabolism such as senile dementia, cerebral infraction, cerebral embolism or peripheral vascular disorder.

Of the powder processed with the existing procedure, the first problem is induction of allergy because of the existing ginkgolic aid, the second is insufficient active ingredient because of the plant cell wall undestructed and the third is impossibility of pass through the blood-brain barrier because of the large particles. This invention has revealed that, with processing *ginkgo biloba* extract with the combination of vapor-phase crushing and liquid-phase crushing, 1) the ginkgolic acid inducing allergy is cleared, 2) the plant cell wall is destructed and 3) the particles are shrunk down to nanosize.

In addition, the novel *ginkgo biloba* extract powder achieved in an animal study enhancement of the release of acetylcholine from the cerebral cortical synapse, improvement of stimulus response of the hippocampal pyramidal cells and reduction of oxidative damage to liver and kidney DNA, with increase of SMP 30 (Senescence Marker Protein-30) in the liver.

Shrinkage of the particle down to nanosized is expected to allow the *ginkgo biloba* extract nanoparticle to flow free, pass through the blood-brain barrier and stimulate directly the brain cells or nerves.

Surface effect reaction of the nanosized particle increased the surface atoms of nanoparticle *ginkgo biloba* extract. Lack of the coordination number of surface atoms induces higher surface ability and the connection with a portion of the brain cell elicits chemical activation, which activates the brain cells.

This invention will provide the novel application of nanoparticle *ginkgo biloba* extract, the activation of the brain cells.

The composition of this invention with the effect of brain function activation is based on the effect of nanoparticle *ginkgo biloba* extract, which facilitates activation of the brain cells, when administered to humans, and which is useful in treatment of the disease possibly mainly from abnormality in cerebral blood flow and metabolism or in improvement of decreased strength or appetite. Abnormality in cerebral blood flow and metabolism is not related only to humans but also to livestock or domestic animals, especially cattle, sheep, pigs, dogs, cats, rabbits, mice, birds and fishes. The composition with the effect of brain function activation from this invention is useful in prevention and treatment of the abnormality in cerebral blood flow and metabolism in these animals.

This invention will provide the composition which is just consumed or administered orally in the form of food additives, food materials, food and drink, health food and drink, drugs, quasi drugs or feeding stuffs to prevent or improve the symptom by the effect of brain function activation.

To take food as an example, this invention will provide the facile way for humans and animals to take the composition with the effect of brain function activation, taking nanoparticle *ginkgo biloba* extract sprinkled into a normal diet.

DETAILED DESCRIPTION OF THE INVENTION

Nanoparticle is usually defined as from single nano (i.e., $\geq 1$ nm, <10 nm) to 100 nm in the narrow sense; it is termed, in the broad sense, wholly including the particles within the nm range ($\geq 1$ nm, <1 $\mu$m) and the subnano range. In this invention, the nanoparitcle is defined as to be several hundred nm and below, optimally 100 nm and below with the narrow sense slightly extended. The nanoparticles used in this operation are 30 nm and 100 nm on average, which are measured by the transmission electron microscope (Hitachi H-9000) according to the testing protocol.

The *ginkgo biloba* extract powder is crushed into the nanoparticles with the breakdown method, the combination of dry and wet processes. For dry ultrafine grinding, the fast-rotating grinder or jet pulverizer for impact attrition, the ball mill, the compression-shearing mill (Ongmill) or the roller mill are used with a classifier. The wet process prevents formation of pulverulent body from accretion and aggregation seen in dry grinding and reduces the cushion effects obstructing atomization, which allows finer grinding than the dry process. The best mode is finally obtaining 30 nm particles by destructing the plant cell walls of *ginkgo biloba* extract powder with the combination of vapor-phase crushing and liquid-phase crushing.

This invention relates to the *ginkgo biloba* extract process utilizing nanotechnology method where the *ginkgo biloba* extract powder is crushed into the fine particles 30 nm on average (FIG. 2) with the breakdown method, the combination of dry and wet process (FIG. 1 Process Chart) by the vapor- and liquid-phase complex crusher made at Tian Li cooperating factory. With the complex grinding, i.e., the dry (vapor-phase) and the wet (liquid-phase) method, the *ginkgo biloba* extract powder is put into the jet flow apparatus where the granulated powder crashes and grinds further with compression and shearing as the following settings are being adjusted: supersonic speed (eg. 340 m/s), high-speed rotation (eg. 15000 turns), heating (eg. 70-80° C.), pressure (250 MPa) and flow rate (eg. 20 kg/h). This is the novel method with which the fine particles of 30 nm are finally obtained and which is the concrete solution to the issues of the existing procedure stated above.

The *ginkgo biloba* extract processed with nanotechnology is characterized by higher biological availability as described below. The nanoparticle of *ginkgo biloba* extract has many distinctive characteristics as in its reactivity or solubility different from the powder. It is marked by the significant increase of reactivity through refinement. The reactivity increase by refinement is derived from the increase of specific surface area and activation level of the particles. The specific surface area of the particle is generally inversely proportional to the particle size. For example, a 1 cm cubic sugar is divided into trillion particles of 1 $\mu$m cubic when the surface area is ten thousands times as large as its original size. A 10 nm across particle has the surface area 100 times as large as that of the 1 $\mu$m particle. Reaction, dissolution, binding or fusion intensifies in proportion directly to the specific surface area of the particle because these effects occur on the particle interface. Besides, the more the particles are shrunk, the more the particles increase their activity, because it increased rate of the atoms on the surface of the particles that is less combinative and reactive. The nanoparticle *ginkgo biloba* extract is small in particle size and its number becomes larger which leads to expansion of the total particle surface area and to high activity of the particles. Furthermore, the nanoparticle *ginkgo biloba* extract is split into smaller in diameter and achieves widespread diffuse in the human body and high biological availability.

The *ginkgo biloba* extract powder processed with nanotechnology has its plant cell wall destructed (FIG. 3 the photograph taken with scanning electron microscope (Hitachi S-3600N) and has the largest release of the active ingredient.

A new discovery is that processing with the nanotechnology changes the form, particle size, of the *ginkgo biloba* extract. It is expected to allow smooth entry of the particle and increased absorption of the *ginkgo biloba* extract. Measurement with the quantum resonance spectrometer CQRS-2 reveals substantial shrinkage of the particle size as shown in Table 1, from which indicates enhancement of the effect to human vessel, blood or cardiac muscle.

TABLE 1

| Measurement Item (Effect on Human Body) | Ginkgo Biloba Extract (Before Nanosized) | Ginkgo Biloba Extract (After Nanosized) |
|---|---|---|
| Cerebral Vessel Thrombus | 4 | 15 |
| Hardened Arteries | 4 | 15 |

TABLE 1-continued

| Measurement Item (Effect on Human Body) | Ginkgo Biloba Extract (Before Nanosized) | Ginkgo Biloba Extract (After Nanosized) |
|---|---|---|
| Blood | 5 | 24 |
| Main Artery | 17 | 29 |
| Cardiac Muscle | 13 | 28 |

Measured with the quantum resonance spectrometer.
>20: significantly beneficial effect
17-20: beneficial effect
14-16: good effect
<14: ordinary effect Ginkgolic acid is a sensitizing substance, which causes contact dermatitis during collection of ginkgo nuts. It is approximately 1.0% contained also in *ginkgo biloba* and the ginkgolic acid and related alkylphenol are usually removed through purification by extraction. This invention showed the extraordinary result that "no ginkgolic acid is detected" in the extract processed with nanotechnology.

Test method 1 *: according to the dietary supplement standard of JHFA.
Test method 2**: according to SHOKUHIN EISEI KENSA SHISHIN [Guideline for Food Hygiene Inspection] (For microorganism) (in Japanese)

The result is as shown in Table 2.

TABLE 2

| Tested Item | Test Result | Detection Limit | Test Method |
|---|---|---|---|
| Flavonoid glycoside | 32.1% | 0.1% | 1* |
| Terpene lactone | 6.2% | 0.1% | 1* |
| Ginkgolide A | 2.0% | — | 1* |
| Ginkgolide B | 0.5% | — | 1* |
| Ginkgolide C | 1.4% | — | 1* |
| Bilobalide | 2.3% | — | 1* |
| Ginkgolic acid | not detected | 1 ppm | 1* |
| Viable count | ≦300/g | — | 2** |

Based on the test data report from Japan Inspection Association of Food and Food Industry Environment As shown by the example, this invention reveals, with the experimental analysis of the *ginkgo biloba* extract processed with nanotechnology, that the extract sample G1 (30 nm on average) administered to the rat enhances the release of acetylcholine from the cerebral cortical synapse and that the extract sample G3 (100 nm on average) to the rat improves the stimulus response of the hippocampal pyramidal cells.

The composition on this invention with the effect improving cerebral blood flow and metabolism has the form chosen from the group consisting of condiments, food additives, food materials, food and drink, health food and drink, drugs, quasi drugs and feeding stuffs, which are combined with the nanoparticle *ginkgo biloba* extract as an active ingredient. It is especially has the form chosen from the group consisting of food additives, food materials, food and drink, drugs and feeding stuffs, which are combined with the nanoparticle *ginkgo biloba* extract as an active ingredient and which may be used for prevention and treatment of the abnormality in the cerebral blood flow and metabolism preventable and improvable by the effect on the flow and metabolism.

The beneficial effect on the cerebral blood flow and metabolism has become utilized in the food claiming the effect as well as drugs.

It can be efficiently used as a food additive providing sweet, taste and/or quality improvement to various condiments: soy sauce, soy sauce powder, bean paste powder, moromi (fermented materials of sake or soy sauce), hishio (flavoring material fermented with rice malt and salt), furikake (rice seasoning), mayonnaise, dressing, vinegar, sambaizu (mixed condiment of vinegar, soy sauce and sweet cooking wine mirin), vinegar powder for sushi, Chinese soup stock, seasoned soy sauce for tempura, seasoned soy sauce for Japanese noodle, Worcester sauce, ketchup, grilled meat sauce, curry roux, stew roux, soup stock, Fish stock powder, composite seasoning, mirin (sweet cooking wine), shin-mirin (mirin flavored condiment with less alcohol), table sugar, coffee sugar.

In addition, it can be efficiently used as a food additive improving the quality of all kinds of food: various Japanese confectionery including rice cracker, cubic rice cracker, okoshi (rice cake packed with syrup), other rice cakes, manju (steamed bean-jam bun), uiroh (steamed cake of rice or flour and sugar), bean-pastes, sweet bean jelly, soft azuki-bean jelly, kingyoku (jellied cake of agar), jelly, castella sponge cake and drop; various western confectionery including bun or bread, biscuit, cracker, cookie, pie, pudding, buttercream, custard, cream puff, waffle, sponge cake, doughnut, chocolate, chewing gum, caramel candy and other candy; water ice including ice cream and sherbet; syrup product including comport and syrup for shaved ice; paste product including flour paste, peanut paste and fruit paste; processed fruits or vegetables including preserve, marmalade, preserved-in-syrup fruit and candied fruit; processed cereal including bread, noodles, rice and artificial meat; pickles including fukujinzuke (minced vegetable pickled in soy sauce and sugar), bettarazuke (radish pickled in rice malt), semmaizuke (pickled turnip) and pickled shallot; pickling liquid or powder such as for radish or Chinese cabbage; livestock food product including ham and sausage; processed fish meat including fish ham, fish sausage, steamed fish paste, chikuwa (fish sausage) and tempura (Japanese deep-fried food); various rare delicacies including sea urchin, fermented squid, vinegared tangle, dried cuttlefish and dried globefish mirinboshi (dipped in sweet sake and dried); layer, wild plants, cuttlefish, fry or seashell boiled in soy sauce; prepared food including boiled bean, potato salad and tangle roll; canned or bottled products of milk products, fish meat, animal meat, fruits and vegetables; alcoholic liquor including synthetic liquor, fruit wine, western liquor and liqueur; soft drinks including coffee, cocoa, canned drink, soda, lactic drink and lactic acid bacteria drink; premix materials such as for pudding or pancake; instants such as of drink, coffee, shiruko (red-bean drink) and soup.

The composition comprising nanoparticle *ginkgo biloba* extract as the active ingredient can be utilized in foods requiring no sweetening: Chinese, Japanese or other noodles made from flour or starch, mashed potato, potato salad or croquette made mostly from potatoes. These foods of carbohydrate (glucide) mask the bitter taste of the nanoparticle *ginkgo biloba* extract and change into the food with the effect improving cerebral blood flow and metabolism when the nanoparticle extract is mixed into the foods for an adult weighing 50 kg to take not over 240 mg nanoparticle extract/day for instance. Besides, it is utilized for the same purpose also in confectionery or bread made mostly from flour, starch or rice powder and requiring no sweetening. As stated above, this invention, the composition comprising nanoparticle *ginkgo biloba* extract as the active ingredient may be used in the very wide range of intake.

The composition chosen from the group consisting of food additives, food materials, food and drink, drugs and feeding stuffs with the effect of brain function activation is characterized to be blended with 0.01-50 wt % nanoparticle *ginkgo biloba* extract. As for the normal composition portions, food and drink may be added the extract of lower limit while it may be added at upper limit provided as a drug, a pill or a capsule. When the composition from this invention, for example as in the form of food and drink is consumed, it will prevent or treat the "abnormality in cerebral blood flow and metabolism," which can be improved or prevented by the effect improving the cerebral blood flow and metabolism.

When the food from this invention is provided as a functional food, it is appropriate to use in the field of the health food preventing abnormality in cerebral blood flow and metabolism. As a health food, it can be combined with optional components such as vitamins, carbohydrate, pigments or flavoring ingredients usually added to foods as well as the essential component nanoparticle *ginkgo biloba* extract. As food, it is consumed in the form of consumers' choice, liquid or solid. It is also consumed in the form of a soft capsule coated with gelatin. The capsule is, for example, made of gelatin coating which is prepared with the raw material gelatin dissolved by water and added the plasticizer such as glycerin or D-sorbitol.

The feeding stuffs from this invention is for livestock, poultry or other domestic creatures such as honeybees, silkworms or fish and is characterized to be the composition blended with 0.01-50 wt % nanoparticle *ginkgo biloba* extract. It is normally used at lower limit of the composition portions while it may be at upper limit when provided as a pill or a capsule.

When these feeding stuffs are administered to livestock, poultry or other domestic creatures such as honeybees, silkworms or fish, it will prevent or treat the "abnormality in cerebral blood flow and metabolism," which can be improved or prevented by the effect improving the cerebral blood flow and metabolism.

When the composition with the nanoparticle *ginkgo biloba* extract is mixed as the active ingredient into the above-mentioned food additives, food materials, food and drink, drugs, quasi drugs and feeding stuffs, the way is just to add the nanoparticle extract so as to account for 0.01-50 wt % at any process by the product completion. To add it, one of the heretofore known processes can be chosen: for example, blending, mixing, dissolution, fusion, immersion, penetration, spreading, coating, covering, spraying, injection, crystallization or caking.

The nanoparticle *ginkgo biloba* extract of this invention is blended into the composition so as to account for 0.01-50 wt %. It may be optimally 0.05-30 and more optimally 0.1-10 wt %. It is preferable, especially in food, drink or feeding stuffs, to be around 0.01-5 wt % though with no limit. Lower than 0.01 wt % of the composition will not provide adequate effect to improve the cerebral blood flow and metabolism while more than 50 wt % is not economically preferable. The *ginkgo biloba* extract must be mixed into other materials so as to be 240 mg/day or low for an adult weighing 50 kg. The content ratio in the composition is determined by the way to consume, eat or administer the relevant composition.

As a drug, it may be administered orally in the form of a capsule, powder or pill. It is soluble in water and other routes such as muscle injection can be adopted as well as oral administration. Injected quantity on intravenous or muscle injection differs by the symptom level of abnormality in cerebral blood flow and metabolism, the body weight, age or sex and it is desired to decide the appropriate quantity according to the case. The content ratio in the drugs is not limited but the administered quantity per 1 kg body weight must be decided for oral administration, intravenous injection or muscle injection with a guide: 240 mg nanoparticle *ginkgo biloba* extract/day or low for an adult weighing 50 kg.

The *ginkgo biloba* extract of this invention has been already used as food and is highly safe. It has a great deal of potential on the cost front when based on the manufacturing method of this invention. In addition, the result of acute oral toxicity testing is "5000 mg/kg or more."

As a drug, the active ingredient, nanoparticle *ginkgo biloba* extract is not only used in itself but also as pharmaceutically acceptable salts thereof. For the relevant agent, the nanoparticle *ginkgo biloba* extract is used as a formulation by itself and, at the same time, as the formulation composition processed from the extract by addition of pharmaceutically available carrier or dilution agent. These formulation or agent compositions may be administered orally or parenterally. The solid or fluid (gel or liquid) formulation or agent composition, for example, has the form of the tablet, capsule, pill, ball, powder, granule or gel preparation. The accurate administered quantity of the formulation or agent composition differs by the usage pattern and treatment time for the purpose and the doctor or veterinarian in attendance determines it. The quantity to take or administer may be appropriately adjusted by the form of the formulation. The daily dose may be taken in one or fractional amounts in the form of oral solid formulation such as pills or oral solution. Besides, for the formulation form of the infant one-shot medicine to act locally or systemically such as syrup, a lozenge or a chewable tablet, the single dose is defined to be one-tenth to half of the daily dose and the total dose need not reach the daily dose.

Meanwhile the amount corresponding to the daily dose may be dispensed as a single dose if it is not an unreasonable quantity for the formulation form. On preparation of the formulation, the dilution agent or vehicle typically used is available including filler, extender, binder, disintegrant, interfacial active agent, lubricant, coating agent or release-sustaining agent. Other additives available as required are solubilization agent, buffer, preservative, solubilizer, tonicity agent, emulsifier, suspending agent, dispersing agent, thickener, gellant, curing agent, absorbent, agglutinant, elasticizer, plasticizer, absorbent, fragrant material, artificial color, flavoring substance, antioxidant, humectant, light shielding agent, brightener or antistatic agent.

Stated differently, the formulation for humans or animals containing the nanoparticle *ginkgo biloba* extract as the active ingredient is administered by itself or in a mixture with vehicles or carriers in the form of injection product, oral agent or suppository. From the vehicles and carriers, the pharmaceutically acceptable ones are chosen and the type and the composition are determined by the administration route and technique. The available carriers in liquid form are, for example, water, alcohols, animal or vegetable oil such as soybean oil, peanut oil, sesame oil or mineral oil or synthetic oil. The available solid carriers are sugars including maltose or sucrose, amino acids, cellulose derivative such as hydroxypropylcellulose or organic salts including magnesium stearate.

The dilution agents for the solid formulation are, for example, flour; starches from potato or corn; sugars including glucose, fructose, sucrose, lactose or oligosaccharide; oilcakes from rice bran or soybean; fish flour; animal matters such as meat meal or skimmed milk; waste cake such as bear yeast or wheat bran; vegetable materials including soybean flour, corn flour or wheat flour; mineral salts including calcium carbonate, calcium phosphate, calcium sulfate or precipitated calcium carbonate. In addition, disintegrant, binding agent or lubricant may be used as required. The available solid formulations include powder medicines, pills, subtle granules, capsules or pellets. Alternatively, it may be dissolved with the appropriate medium such as distilled water, normal saline or dextrose in water and solubilizing agent as required and can be used as injection solution.

The formulation of this invention is intended for human or animal use and may be administered to the animals such as sheep, cattle, horses, pigs, goats, dogs, cats, ferrets, rodents including mice or rats, chickens, birds including geese or turkeys, marsupials, fishes, primates or reptiles. It may be administered orally in the form of the oral formulation or in a mixture with feeding stuffs or drinking water. The injection solution may be administered to any regions including subcutaneous, muscle, vein or abdominal cavity. The applied dose of any formulations includes 240 mg active ingredient or low per day for an adult weighing 50 kg as a standard.

The composition of this invention may be used as a component of the external skin preparation. The external preparation hereat is not specified but widely includes drugs, quasi drugs, cosmetic materials such as beauty products or toiletries: specifically, skin toner, facial cream, emulsion, facial mask, foundation, cosmetic oil, ointment, gel, deodorant, hair growth tonic, hair mist, hair gel, shampoo, hair conditioner, face wash or body wash. As to the *ginkgo biloba* extract content in the external skin preparation, in terms of efficacy, the appropriate ratio of the dry solid extract is generally 0.01-30 wt %, optimally 0.1-20 wt % and more optimally 0.5-10 wt % so as to be 240 mg intake or low per day for an adult weighing 50 kg.

The external skin preparation of this invention synergistically reduces skin inflammation in combination with anti-inflammatory drugs. The optimal examples of anti-inflammatory drugs are glycyrrhetinic acid, glycyrrhizinic acid and its derivative, mefenamic acid, allantoin, vitamin E, Vitamin C and its derivative, aminocaproic acid, guaiazulene and its derivative and salt such as sodium guaiazulene sulfonate and zinc oxide.

The external skin preparation of this invention can contain, besides the *ginkgo biloba* extract, one or more from: glycyrrhetinic acid, dipotassium glycyrrhizinate, tocopherol acetate, guaiazulene, sodium ascorbate, aminocaproic acid, licorice extract, aloe extract, rosemary extract, *scutellaria* root extract, green tea extract, horse chestnut extract, seaweed extract, horsetail extract, *pinus sylvestris* cone extract, hop extract, lemon extract, *ruscus aculeatus* root extract, arnica extract, hamamelis water, mulberry root extract, fermented rice extract, *lithospermum erythrorhizon* extract, *sapindus mukurossi* peel extract and *eucalyptus* extract.

The external skin preparation of this invention can contain one or more than one of the above anti-inflammatory drugs or botanical extracts and the content is generally 0.0001-5 wt % and optimally 0.01-3 wt %.

The external skin preparation of this invention may contain the base material according to the preparation form. Specifically, it may be mineral oil, animal or plant oil, wax, fatty acid, fatty alcohol, ester oil, surfactant, humectant, high polymer, animal or botanical extract, amino acids, solvent, antiseptic, ultraviolet absorber, sequestrant, antioxidant, pH adjuster, pigment or colorant or flavoring ingredient and it can be blended as far as it does not detract from the effect of this invention. Here are their specific examples.

<Mineral Oil>

Liquid paraffin, Liquid isoparaffin, etc.

<Animal/Vegetable Oil>

Squalane, Olive oil, Camellia oil, Wheat germ oil, Jojoba oil, Avocado oil, Carrot oil, Shea butter, Palm oil, Hardened oil, Horse oil, Lanolines, Egg yolk oil, Cloves oil, Rose hip oil, Lavender oil, Mentha oil, Spearmint oil, Rosemary oil, etc.

<Wax>

Microcrystalline wax, Solid paraffin, Yellow beeswax, etc.

<Fatty Acid>

Lauric acid, Myristic acid, Palmitic acid, Stearic acid, Oleic acid, Isostearic acid, etc.

<Fatty Alcohol>

Lauryl alcohol, Myristyl alcohol, Cetanol, Cetostearyl alcohol, Stearyl alcohol, Isostearyl alcohol, Oleyl alcohol, Hexyldecanol, Behenyl alcohol, Octyldodecanol, Lanolin alcohol, etc.

<Ester Oil>

Caprylic triglyceride, Cetyl 2-ethylhexanoate, Glyceryl tri-2-ethylhexanoate, Isocetyl octanoate, Isononyl Isononanoate, Ethylene glycol diethylhexanoate, Caprylic/capric triglyceride, Isopropyl myristate, Isopropyl palmitate, Isocetyl myristate, Cetyl palmitate, Dialkyl carbonate, etc.

<Surfactant>

Sodium lauryl sulfate, Alkyl sulfate, Polyoxyethylene alkyl sulfate, Tetradecene sulfonate, Polyoxyethylene alkylsulfo succinate, Sodium lauroyl sarcosinate, Alkyl methylalanine sodium salt, Polyoxyethylene alkyl ether phosphate, Fatty-acid soap, N-acyl-glutamate, Lauric acid diethanolamine, Coconut oil fatty acid diethanolamine, Alkyldimethyl amine oxide, Alkyl methyl taurine sodium salt, Alkyl aminopropionic acid sodium salt, Polyoxyethylene alkyl ether carboxylate, Alkyl Phosphate, Alkylglucoside, Polyether modification silicon, etc.

Alkyl trimethylammonium chloride, Alkyl trimethylammonium bromide, Amide amine, Dialkyl dimethyl ammonium chloride Alkyldimethyl betaine acetate, Alkylamide propyl betaine, Alkylcarboxy methyl hydroxy ethyl imidazolinium betaine Lecithin (soybean or egg-yolk) derivative, Propylene glycol fatty acid ester, Glycerine fatty acid ester, Polyoxyethylene glycerine fatty acid ester, Polyglycerol fatty acid ester, Sorbitan fatty acid ester, Polyoxyethylene sorbitan fatty acid ester, Polyoxyethylene sorbit fatty acid ester, Polyoxyethylene hardened castor oil, Polyethylene glycol fatty acid ester, Polyoxyethylene alkyl ether, Polyoxyethylene polyoxypropylene alkyl ether, Polyoxyethylene alkyl nonylphenyl ether, Polyoxyethylene alkyl ether phosphoric acid/phosphate <Humectant>

Propylene glycol, Dipropylene Glycol, 1,3-Butylene glycol, Glycerin, Diglycerin, Isoprene glycol, Polyethyleneglycol, Sorbit, Maltitol, Trehalose, Xylitol, etc.

<High Polymer>

Methylcellulose, Ethylcellulose, Carboxymethylcellulose, Hydroxyethylcellulose, Hydroxypropylcellulose, Carboxy vinyl polymer, Polyvinyl alcohol, Polyvinylpyrrolidone, Cationized cellulose, Cationized guar gum, Sodium hyaluronate, Sodium polyacrylate, Xanthan Gum, Carrageenan, etc.

<Animal/Botanical Extract>

Placenta extract, Hydrolyzed collagen, Hydrolyzed keratin, Hydrolyzed silk, Hydrolyzed elastin, Yeast extract, Aloe extract, *Symphytum officinale* leaf extract, Peony root extract, *Perilla* extract, Sialid extract, Hamamelis water, *Isodonis japonicus* extract, Hops extract, Sage leaf extract, Horse chestnut extract, Peach leaf extract, *Saxifraga sarmentosa* extract, Balm mint leaf extract, Mogwort extract, Rosemary leaf extract, Rice bran ferment extract, etc.

<Amino Acids>

L-alanin, L-arginine, L-asparatic acid, L-glutamine, L-cysteine, L-serine, L-tyrosine, L-proline, Pyrrolidone carboxylate, Glycine, etc.

<Solvent>

Purified water, Aqua, Ethanol, Isopropanol, Benzyl alcohol, etc.

<Vitamin Group>
Vitamin A, Retinol acetate, Pyridoxine hydrochloride, Pyridoxine dicaprylate, Biotin, Nicotine acid, Nicotinic-acid amide, Benzyl nicotinate, Riboflavin, Calcium pantothenate, D-Pantothenyl alcohol, Ascorbic acid, Ascorbyl palmitate, Magnesium-L-ascorbyl-phosphate, Ergocalciferol, Vitamin E, Tocopherol acetate, Natural vitamin E, etc.

<Antiseptic>
Methylparaben, Ethylparaben, Propylparaben, Butylparaben, Isobutylparaben, Phenoxyethanol, Bisabolol, Hinokitiol, Benzoic acid, Sodium benzoate, Salicylic acid, Sodium salicylate, Sorbic acid, Potassium sorbate, Undecylenic acid, Pionin, l-menthol, d-camphor, etc.

<Ultraviolet Absorber>
Para-aminobenzoic acid, Ethyl para-aminobenzoic acid, Glyceryl para-aminobenzoic acid, 2-ethylhexyl paradimethylaminobenzoate, Oxybenzone, Dihydroxy benzophenone, Dihydroxy-dimethoxy benzophenone, Dihydroxy dimethoxybenzophenone sulfonate, Hydroxy methoxybenzophenone sulfonate, Octyl salicylate, etc.

<Sequestrant>
Edetic acid, Edetate, Ethylene diamine hydroxyethyl triacetic acid trisodium, Diethylene triamine pentaacetic acid, Diethylene triamine pentaacetic acid pentasodium, Tetrakis (2-hydroxypropyl) ethylenediamine dioleate, Hydroxy ethanedisulfonate, Hydroxy ethanedisulfonate tetrasodium, Phytic acid, etc.

<Antioxidant>
Dibutylhydroxytoluene, Butylhydroxyanisol, Erythorbic acid, Propyl gallate, Octyl gallate, Tocopherol, etc.

The external skin preparation of this invention can be manufactured according to the common procedure depending on its form.

The details of this invention are provided below with examples. This invention is not to be considered limited by these examples.

EXAMPLE 1

Manufacturing Method of Nanoparticle *Ginkgo Biloba* Extract

The common *ginkgo biloba* extract has been conventionally manufactured based on the following flow chart.

material→extraction distillation→(solvent exchange to hexane)→concentration→purification with hydrophobic adsorbent resin→desorption→distillation purification with hydrophobic adsorbent resin→concentration→drying product (powder)

On this invention, the *ginkgo biloba* extract is manufactured at Tian Li cooperating factory with the conventional method where the *ginkgo biloba* is extracted by alcohol and the extract is concentrated by adsorption with adsorbent resin, dried at a high temperature and powderized into 200 mesh), by which the *ginkgo biloba* extract sample G2 (200 mesh) is obtained.

The nanoparticles are prepared as below.

The *ginkgo biloba* extract powder is diluted with water (concentration: 20 wt %) and injected into the funnel of vapor-phase crusher (Tian Li cooperating factory made). The liquid flows into the refinement room by gravitation and passes through the microfiltration membrane as the flow volume and emulsion minuteness are adjusted. High pressure (200 MPa), high-speed rotation (15000 turns), supersonic speed (340 m/s) and heating (70-80° C.) are applied in the airflow room, where the flow enters into the five inlets at the bottom of the unit. The granulated powder is caught in the fast air stream and crushed by intercollision. The particles passed are discharged from the outlet at the top of the unit and the rejected particles are returned to the refinement room to be crushed again.

The discharged particle (approx. 500 nm) are directly led into the jet-flow room of the liquid-phase crusher (Tian Li cooperating factory made) and through the intensifier, which increases the pressure with the high pressure air (250 MPa), to be blown out at high speed from the outlet of the injector toward the board inside the unit. The granulated powders collide against the board at high speed and become gradually reduced in size until tinier particles (approx. 30 nm on average) as the board is applied supersonic vibration from the high-speed impact. The particles are subsequently cleansed in the clean room and dried off with the spray drier to be powder form. The last process is collecting the nanoparticles into the powder collection room. The *ginkgo biloba* extract sample G1 [30 nm: measured by the transmission electron microscope (Hitachi H-9000)] is obtained through the above procedure.

Besides, the *ginkgo biloba* extract sample G3 (100 nm) is also obtained with the same nanotechnology.

The *ginkgo biloba* extract prepared with nanotechnology as shown in this example is utilized to carry out the experiments of the following examples 2-5.

EXAMPLE 2

Enhancement of Acetylcholine Release from the Cerebral Cortical Synapse

The test procedure and the analysis data from the animal experiment are indicated below.

Male Wistar rats (average weight: 409 g) at 27 months were included in the study. Handling was continued from one week before administration in order to decrease the stress from administration. The *ginkgo biloba* extract samples: G1 (30 nm), G2 (200 mesh) and G3 (100 nm) are suspended in water (1.96 mg/0.25 mL) and the suspension is administered (240 mg/50 kg wt) using a stomach sonde, feeding needle once a day (n=4/group). The control rats (n=5) were administered water. The duration of administration is one month and throughout which they were allowed to free access to solid feed and drinking water.

Synaptosomes were prepared from the cerebral cortices of the rats using Ficoll discontinuous density gradient centrifugation method.

Synaptosomes were suspended in Krebs-Ringer solution containing 200 µM eserine (acetylcholinesterase inhibitor) and it was incubated at 37° C. for 30 min. At the end of the incubation, the reaction was stopped by adding 0.1 N perchloric acid. After addition of known quantity of ethylhomocholine, EHC as an internal standard, it was centrifuged to obtain the supernatant.

Some of the synaptosomes incubated at 37° C. for 30 min was washed with Krebs-Ringer solution containing eserine and then additionally suspended in the buffer solution. The Krebs-Ringer solution containing concentrated potassium was added to this suspension to adjust the final potassium levels to be 10 mM and 40 mM and it was incubated at 37° C. for 5 min. After that it was added EHC and centrifuged to obtain the supernatant. From these samples, ACh synthesis and release were estimated with the high performance liquid chromatography system with the electrochemical detector (EICOM 300).

Experimental Discussion

Here are the results and discussion of Example 2 out of the above experiments.

FIG. 4 shows administration effect of each *ginkgo biloba* extract sample on ACh synthetic activity in the cerebral cortical synapse. The ACh synthetic activity in the rats treated with the *ginkgo biloba* extract is approximate equivalent that of the control rats, from which every sample of the *ginkgo biloba* extract is considered not to have effect on ACh synthetic activity in the cerebral cortical synapse.

Next the effect of depolarizing stimulation by the concentrated potassium on ACh release in the synapse is studied (FIG. 5). The rats treated with the *ginkgo biloba* extract show more promotion of ACh release in the cerebral cortical synapse than the control rats. The significant release of ACh is particularly observed in the rats treated with G1.

Experimental Results

The results of Example 2 suggest that the *ginkgo biloba* extract promotes ACh release efficiency by depolarizing stimulation without promoting ACh synthetic activity in the brain synapses of aged rats.

EXAMPLE 3

Improving Effect of Stimulus Response of Hippocampal pyramidal Cells

The hippocampus was removed and cut into 400 μm-thick slices using a rotary slicer. The slices were incubated for 2 hours in the artificial cerebrospinal fluid (ACSF) in which the gas mixture (95% $O_2$+5% $CO_2$) was dissolved enough and were subjected to the experiment. After the hippocampus slices were placed into the assay camber, the stimulating electrode was inserted into Schaffer collaterals and the recording electrode into the pyramidal cell layer and the stratum radiatum of CA1. The electrical pulse stimulation was applied once per 10 sec and the population spikes and the excitatory postsynaptic potentials were recorded. After verifying stable baseline, the response to the varying stimulus intensities was measured as the electrical pulse stimulation was changed between 0.04 mA and 0.25 mA.

Experimental Discussion

FIG. 6 shows the amplitudes of the population spikes in the hippocampal CA1 pyramidal cell layer. It was demonstrated that the amplitudes were greater in the group given the *ginkgo biloba* extract than in the control group. The significant amplification of the population spikes was noted especially in the rats treated with G3. The group given the *ginkgo biloba* extract presented the greater increasing trend of the excitatory postsynaptic potential (EPSP), the indicator of neuronal excitability, than the control group. It is considered to be the result suggesting that administration of the *ginkgo biloba* extract increased the hippocampal pyramidal cell response to stimulation or increased the cell population which responds to stimulation.

Experimental Results

The results of Example 3 revealed that the *ginkgo biloba* extract sample G3 improves the stimulus response of the hippocampal pyramidal cells and has the effect of neuron activation in the hippocampus.

EXAMPLE 4

Effect Against Oxidative DNA Damage

From the analysis experiment for antiaging effect of the *ginkgo biloba* extract processed with nanotechnology, here are the results on the effect against the oxidative damage to the liver and kidney DNA of the aged rats.

By measurement of the DNA oxidative damage markers, the extent of the oxidative damage in the liver and kidney of the rats treated with the nanotechnology-processed novel *ginkgo biloba* extract samples.

The liver and kidney were removed from 27-month Wistar rats administered with the *ginkgo biloba* extract for one month, from which the nuclear DNA was extracted and the oxidative damage markers (8-oxodeoxyguanosine: 8-oxodG) were quantified using HPLC/ECD (electrochemical detector). Grouping was as follows: Control (n=5), Group 1 (n=2), Group 2 (n=3) and Group 3 (n=2).

The nuclear DNA was separated using the reported method. The tissue (ca. 150 mg) was homogenized in 0.3 M sucrose solution and centrifuged to remove the cytosolic fraction with mitochondria. The pellets were incubated in the mixture of proteinase K and SDS/EDTA (pH 8.0) under an argon atmosphere and added 7M sodium iodide and isopropyl alcohol and then the mixture was centrifuged. The DNA pellets were dissolved in 0.01×SSC/EDTA and incubated with the mixture of ribonuclease Ti and A under an argon atmosphere. The sample was extracted with the mixture of chloroform and isoamyl alcohol (24:1, v/v). The water phase was mixed with sodium iodide and isopropyl alcohol and the mixture was left to stand at −20° C. The mixture was centrifuged and the DNA pellets were washed with 40% isopropyl alcohol and 70% (v/v) ethanol and then dissolved in Chelex 100 solution. The amount and purity of DNA were determined by UV absorption as reported previously.

The DNA was hydrolyzed with nuclease P1 and alkaline phosphatase under an argon atomosphere and 8-oxodG was quantified using HPLC system with Symmetry C18 columns and ESA Coulochem II 5200 electrochemical detector (ECD).

8-oxodG content was expressed as the molar ratio to $10^5$ 2'-deoxyguanosine (dG). The amount of dG was calculated from the absorbance of the sample at 260 nm measured by the UV detector.

Experimental Results

While significant differences are not expected in the steady state, the results of Example 4 shows the reduction of the DNA oxidative damage markers in the livers and kidneys of Group 1 (FIG. 7).

EXAMPLE 5

Increase of SMP 30 Protein Amount in the Liver

The homogenates were prepared and the immunoblotting assay was performed here. The livers and kidneys from the rats treated with the novel *ginkgo biloba* extract and the control rats were added the ice-cold buffer solution for homogenization: 10 mM Tris-HCl (pH 8.0), 1 mM DTT (dithiothreitol), 1 mM PMSF (phenylmethanesulfonyl fluoride) and then homogenized at high speed for 30 sec using a Polytron homogenizer. The homogenate was centrifuged at 10,000×g for 30 min. The protein was purified from the supernatant (7.5 μg) obtained from the livers and kidneys of the rats treated with the novel *ginkgo biloba* extract and the control rats and was analyzed by SDS-PAGE using 4-20% gradient gel (Daiichi Pure Chemicals Co., Tokyo, Japan). The protein concentrations were determined using bovine serum albumin as a standard substance with BCA protein assay reagent (Pierce Biotechnology, Inc., Rockford, Ill., USA). The proteins were electronically transferred to the nitrocellulose membrane. The SMP 30 of the rats were detected with the polyclonal rabbit antibody (dilution 1:5000). The markers were detected using ECL Westernblotting detection reagent (Amersham Biosciences Corp.) with anti-rabbit IgG conjugated with horseradish (dilution 1:5000, BIO RAD) as the second antibody. The bands corresponding to SMP 30 were photographed with LAS-3000mini (FUJIFILM) and quantified.

The SMP 30 in the soluble fraction of the livers was detected by Western blotting using polyclonal antibody and the bands were quantified with the analysis software. The results are as shown in Table 3.

TABLE 3

4 per group

| Treated Group | Organ Liver | | | |
|---|---|---|---|---|
| | Cont | Ginkgo 1 | Ginkgo 2 | Ginkgo 3 |
| Rate of Change of SMP 30 Amount (%) | 100 | 86 | 85 | 172 |
| SE | 4 | 6 | 8 | 35 |

FIG. 8 shows the rate of change of SMP 30 protein amount in the livers of the treated rats and reveals the SMP 30 increase in the rats treated with G3.

Experimental Results

The results of Example 5 reveal the SMP 30 increase in the rats by the measurement of change of SMP 30 protein amount in the livers.

The *ginkgo biloba* extract processed with the double crushing method (vapor-phase and liquid-phase crushing) appears in the nano-level particle and has the novel capability, and so it is expected to have great industrial applicability in the future. Shrinkage of the particle down to nanosized is expected to allow the *ginkgo biloba* extract nanoparticle to flow free, pass through the blood-brain barrier and stimulate directly the brain cells or nerves. Surface effect reaction of the nanosized particle increased the surface atoms of nanoparticle *ginkgo biloba* extract. Lack of the coordination number of surface atoms induces higher surface ability and the connection with a portion of the brain cell elicits chemical activation, which activates the brain cells.

BRIEF DESCRIPTION OF THE DRAWINGS

FIG. 8 is a bar graph showing the change of SMP 30 protein amount in the livers.

Figure 1:
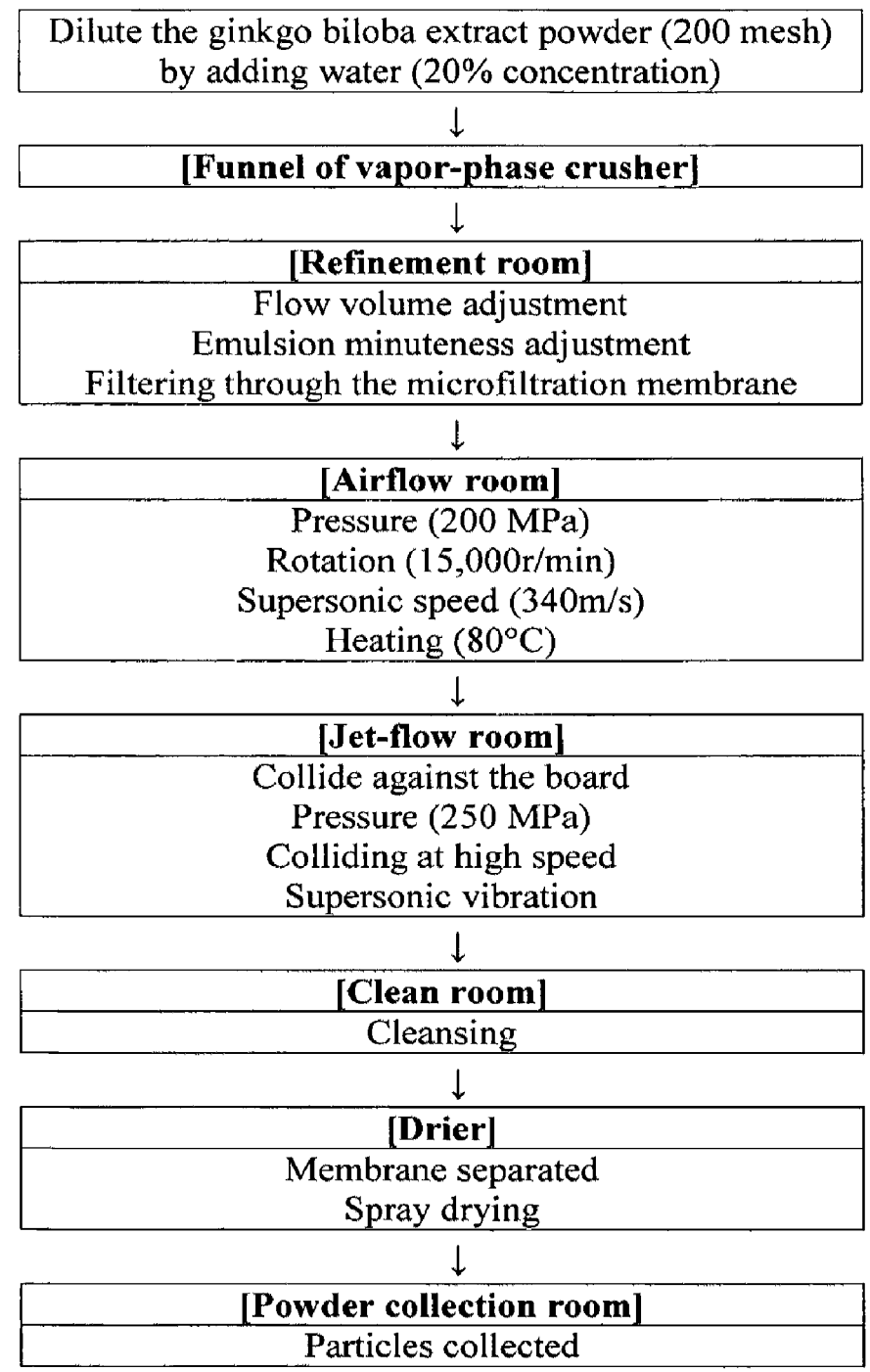
FIG. 1 shows process chart of nanosizing of the *ginkgo biloba* extract powder.
Figure 2:
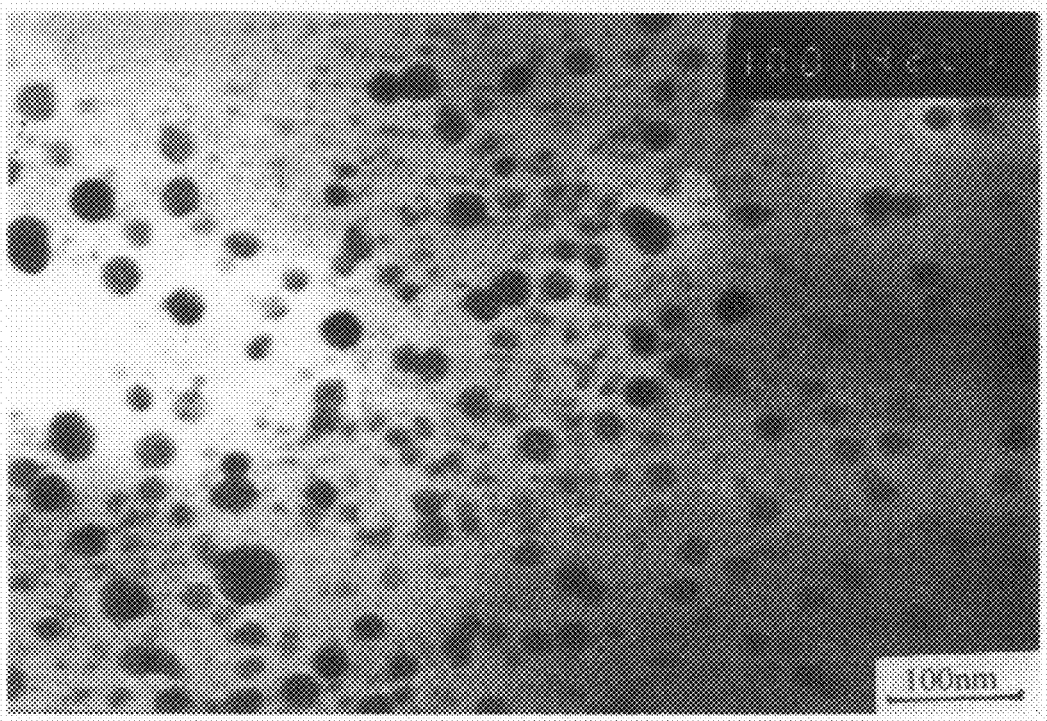
FIG. 2 shows micrograph of the *ginkgo biloba* extract processed into 30 nm particles by the liquid-phase crushing, which was taken by the transmission electron microscope (Hitachi H-9000).
Figure 3:
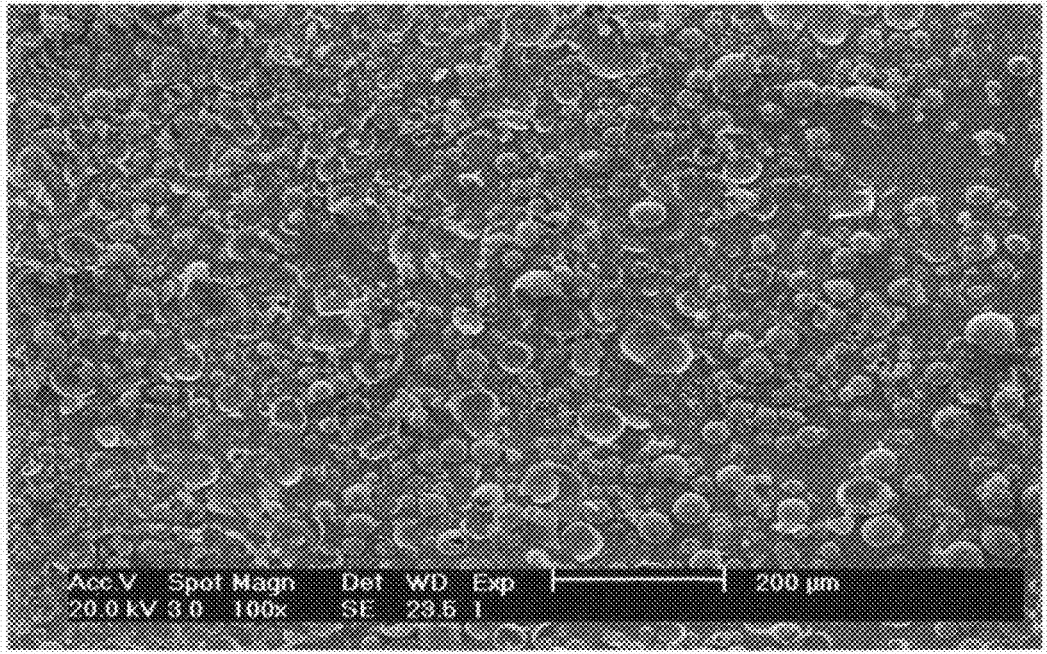
FIG. 3 shows micrograph of the *ginkgo biloba* extract powder processed by the vapor-phase crushing, destructing the plant cell wall, which was taken by the scanning electron microscope (Hitachi S-3600N).
Figure 4:
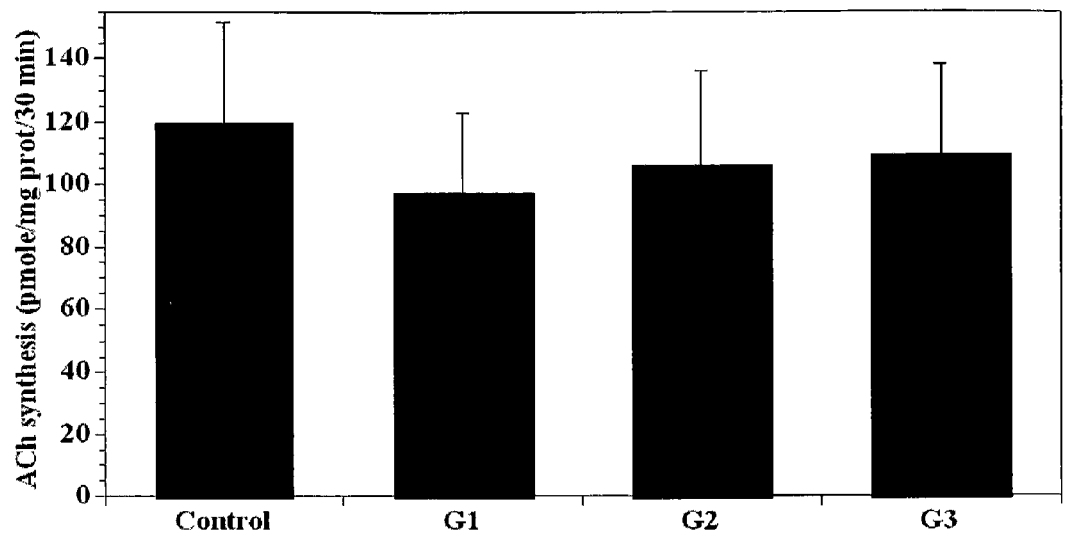
FIG. 4 is a bar graph showing the dose effect of the *ginkgo biloba* extract on ACh synthetic activity in the cerebral cortical synapse.
Figure 5:
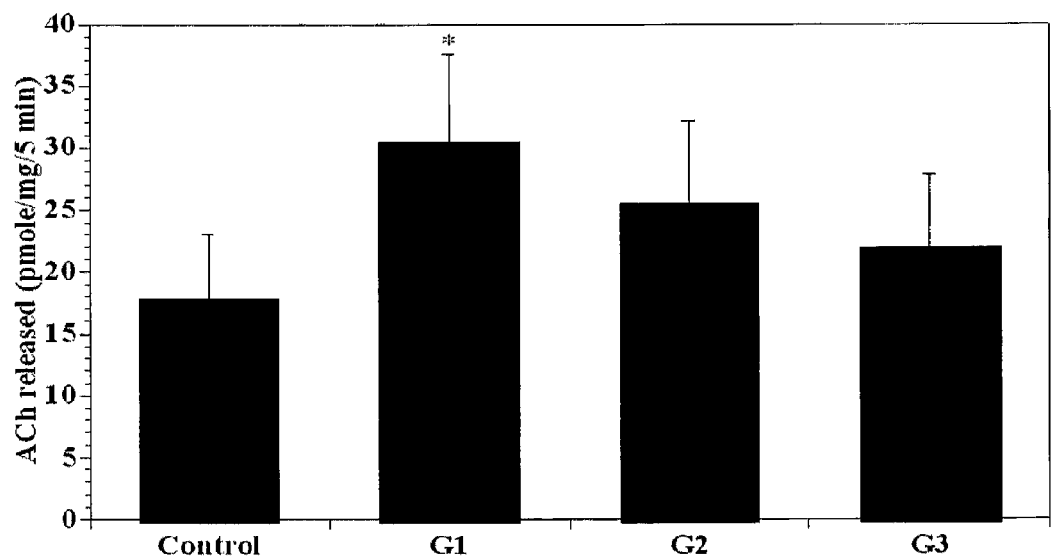
FIG. 5 is a bar graph showing the dose effect of the *ginkgo biloba* extract on ACh release in the cerebral cortical synapse.
Figure 6:
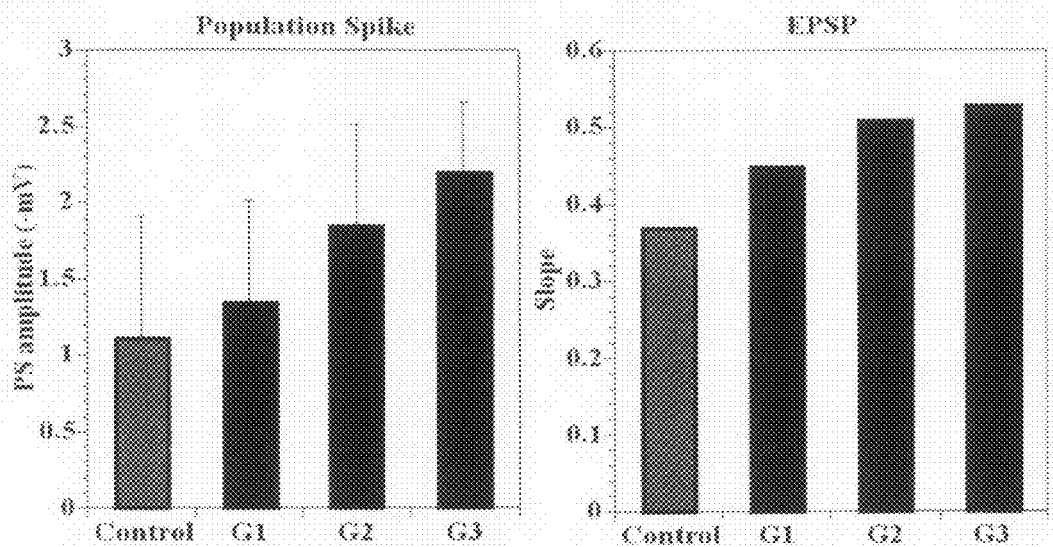
FIG. 6 is a bar graph showing the hippocampal pyramidal cell response to stimulation.
Figure 7:
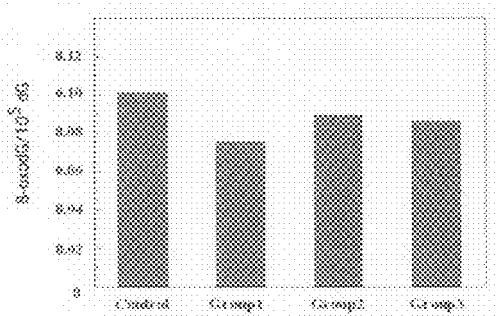
FIG. 7 is a bar graph showing the measurement of the DNA oxidative damage markers in the livers and kidneys.
Figure 7:
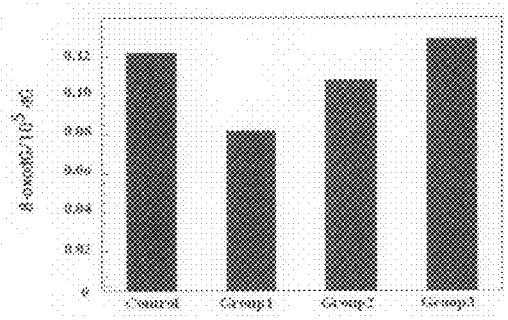

What is claimed are defined as follows:

1. A method for producing a *ginkgo biloba* extract product, comprising:

obtaining a starting material comprising starting *ginkgo biloba* extract particles having a particle size larger than 100 nm;

crushing the starting *ginkgo biloba* extract particles to produce *ginkgo biloba* extract particles have an average particle size of between about 30 nm and about 100 nm, including:

(a) introducing the starting *ginkgo biloba* extract particles into an airflow room and applying a high pressure of about 200 MPa, a high-speed rotation of about 15000 turns, and heat of about 70-80 degree C. in the airflow room, whereby the starting *ginkgo biloba* extract particles are caught in air streams and crushed by intercollision; and (b) blowing the particles obtained from step (a) at a high speed toward a board inside a jet-flow room, whereby the particles collide against the board at a high speed and become reduced in size; and collecting the *ginkgo biloba* extract particles as the *ginkgo biloba* extract product.

2. The method of claim 1, wherein the starting *ginkgo biloba* extract particles have a particle size of about 200 mesh.

3. The method of claim 1, wherein the particles obtained from step (a) have an average particle size of about 500 nm and the particles obtained from step (b) have an average particle size of about 30 nm to about 100 nm.

4. The method of claim 1, wherein the crushing step further comprises:

before step (a), (c) diluting the starting *ginkgo biloba* extract particles with a liquid; and (d) passing the diluted *ginkgo biloba* extract particles through a microfiltration membrane.

5. The method of claim 1, wherein the crushing step further comprises:

(e) cleansing the particles obtained in step (b); and (f) drying the cleansed particles from step (e) using a spray drier.

* * * * *